United States Patent
Goldstein et al.

[11] Patent Number: 6,034,250
[45] Date of Patent: Mar. 7, 2000

[54] NITRONE COMPOUNDS

[75] Inventors: Solo Goldstein, Suresnes; Alain Dhainaut, Chatou; André Tizot, Verruieres le Buisson; Brian Lockhart, Croissy sur Seine; Pierre Lestage, La Celle Saint Cloud, all of France

[73] Assignee: Adir Et Compagnie, Courbevoie, France

[21] Appl. No.: 09/340,088

[22] Filed: Jun. 25, 1999

[30] Foreign Application Priority Data

Jun. 26, 1998 [FR] France ................................. 98 08116

[51] Int. Cl.⁷ ..................... C07D 233/66; C07D 233/90; A61K 31/415
[52] U.S. Cl. .................. 548/336.1; 514/399; 514/400
[58] Field of Search ............ 548/336.1; 514/399, 514/400

[56] References Cited

U.S. PATENT DOCUMENTS 4,803,282 2/1989 St Georgiev et al. ........... 548/336.1 X

FOREIGN PATENT DOCUMENTS 62-175469 8/1987 Japan .................................. 548/336.1

*Primary Examiner*—Floyd D. Higel
*Attorney, Agent, or Firm*—The Firm of Gordon W. Hueschen

[57] ABSTRACT

A compound selected from those of formula (1):

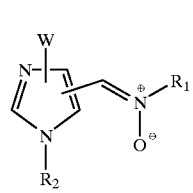

wherein

W represents aryl, arylalkyl, heteroaryl, or heteroarylalkyl, each being optionally substituted, $R_1$ represents alkyl, alkenyl, alkynyl, aryl, cycloalkyl, arylalkyl, or cycloalkylalkyl, each being optionally substituted.

$R_2$ is as defined in the description, its isomers, and addition salts thereof with a pharmaceutically-acceptable acid or base, and medicinal products containing the same which are useful as anti-oxidation agents.

12 Claims, No Drawings

NITRONE COMPOUNDS

FIELD OF THE INVENTION

The present invention relates to new nitrone compounds. These new compounds are antioxidants, traps for reactive oxygenated species, which are capable of combating "oxidation stress" in the cerebral region.

According to Hartman's free-radical theory of ageing, successive oxidation attacks create "oxidation stress" conditions, that is to say create an imbalance between the protective systems in favour of the pro-oxidants.

Such attacks result in numerous molecular modifications, especially of polyunsaturated membrane lipids, proteins and nucleic acids. Human and animal organisms possess various defence mechanisms that act in synergy. Those mechanisms are of an enzymatic nature (superoxide dismutase, catalase, glutathione peroxidase) or of a non-enzymatic nature (such as vitamins E and C, which enable physiological control of free-radical activity). With age, however, that protection becomes less efficient, not to say inefficient, especially as a result of the oxidative inactivity of a large number of enzymes including those involved in such defence mechanisms. Consequently, for some disorders associated with ageing, such as atherosclerosis, cataract, non-insulin-dependent diabetes, cancer or chronic neurodegenerative disorders, numerous studies have been able to demonstrate that such conditions are associated with those "oxidation stress" conditions.

The central nervous system is especially sensitive to "oxidation stress" because of its high oxygen consumption, the relatively low levels of its anti-oxidation defences and the high iron content of some cerebral regions. This explains why "oxidation stress" might be one of the main etiological factors of cerebral ageing, as well as of chronic neurodegenerative disorders, especially Alzheimer's disease and neurodegeneracies of the basal ganglia.

Various free-radical traps that act as anti-oxidation agents have been described in the literature. This applies more especially to the compounds described in Patent Application WO 92/22290.

In addition to the fact that the compounds of the present invention are new, they have proved to be more powerful antioxidants that those described in the literature, and to be non-toxic. Advanced theoretical HOMO/LUMO calculations demonstrate the characteristics of these products in terms of their efficiency in trapping free radicals that are either carbonated (LUMO low) or oxygenated (HOMO high). Those characteristic properties hence render the compounds of the invention of potential use in the treatment and prevention of pathologies that on the one hand are associated with ageing, especially cerebral ageing, and that on the other hand result from oxidation stress.

The compounds of the invention accordingly constitute therapeutic agents that can be used as anti-oxidation agents and that are capable of combating cognitive disorders associated with cerebral ageing or neurodegenerative disorders, and also combating neurone death associated not only with acute neurodegenerative disorders such as, for example, ischaemia and epilepsy, but also with progressive neurodegenerative disorders, such as, for example, Alzheimer's disease, Pick's disease or neurodegeneracies of the basal ganglia.

DETAILED DESCRIPTION OF THE INVENTION

More specifically, the present invention relates to compounds of formula (1):

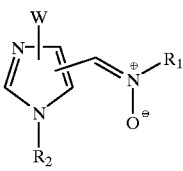

(I)

wherein

W represents an aryl group, an aryl-$(C_1-C_6)$alkyl group in which the alkyl moiety may be linear or branched, a heteroaryl group or a heteroaryl-$(C_1-C_6)$alkyl group in which the alkyl moiety may be linear or branched, $R_1$ represents a linear or branched $(C_1-C_6)$alkyl group, a linear or branched $(C_2-C_6)$alkenyl group, a linear or branched $(C_2-C_6)$alkynyl group, an aryl group, a cycloalkyl group, an aryl-$(C_1-C_6)$alkyl group in which the alkyl moiety may be linear or branched, or a cycloalkyl-$(C_1-C_6)$alkyl group in which the alkyl moiety may be linear or branched, $R_2$ represents a hydrogen atom, a linear or branched $(C_1-C_6)$alkyl group, an aryl group, an aryl-$(C_1-C_6)$alkyl group in which the alkyl moiety may be linear or branched, a cycloalkyl group, a cycloalkyl-$(C_1-C_6)$alkyl group in which the alkyl moiety may be linear or branched, a heterocycloalkyl group, a heterocycloalkyl-$(C_1-C_6)$alkyl group in which the alkyl moiety may be linear or branched, a heteroaryl group, a heteroaryl-$(C_1-C_6)$alkyl group in which the alkyl moiety may be linear or branched, a linear or branched $(C_1-C_6)$acyl group, a linear or branched $(C_1-C_6)$alkylsulphonyl group, an arylsulphonyl group, an aryl-$(C_1-C_6)$alkylsulphonyl group in which the alkyl moiety may be linear or branched, or a linear or branched $(C_2-C_6)$alkenyl group, their isomers, and also additions salt thereof with a pharmaceutically acceptable acid or base.

Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic and camphoric acid etc.

Amongst the pharmaceutically acceptable bases there may be mentioned, without implying any limitation, sodium hydroxide, potassium hydroxide, triethylamine, tezibutylamine etc.

"Cycloalkyl" is to be understood as meaning a mono- or bi-cyclic group that is saturated or unsaturated but is not aromatic and that contains from 3 to 10 carbon atoms, it being possible for each of those groups to be substituted by one or more identical or different substituents selected from halogen atoms, hydroxy groups, linear or branched $(C_1-C_6)$ alkyl groups, linear or branched $(C_1-C_6)$alkoxy groups, linear or branched $(C_1-C_6)$acyl groups, amino groups (wherein amino is itself optionally substituted by one or two identical or different linear or branched $(C_1-C_6)$alkyl groups), linear or branched $(C_1-C_6)$alkoxycarbonyl groups, mercapto groups and linear or branched $(C_1-C_6)$alkylthio groups.

"Heterocycloalkyl" is to be understood as meaning a cycloalkyl group in which one, two or three carbon atoms have been replaced by identical or different hetero atoms selected from nitrogen, oxygen and sulphur.

"Aryl" is to be understood as meaning a phenyl, naphthyl, indenyl, tetrahydronaphthyl, dihydronaphthyl or dihydroindenyl group, each of which is optionally substituted by one or more identical or different groups Q, Q representing a halogen atom or one of the following groups: hydroxy, cyano, nitro, linear or branched ($C_1$-$C_6$)alkyl, aryl, heteroaryl (it being understood that when Q represents an aryl or heteroaryl group, then the said aryl group or the said heteroaryl group may not be substituted by another aryl or heteroaryl group), linear or branched ($C_1$-$C_6$)alkoxy, linear or branched trihalo-($C_1$-$C_6$)alkyl, linear or branched trihalo-($C_1$-$C_6$)alkoxy, linear or branched ($C_1$-$C_6$)acyl, carboxy, linear or branched ($C_1$-$C_6$)alkoxycarbonyl, linear or branched ($C_1$-$C_6$)alkylcarbonyloxy, amino (optionally substituted by one or two identical or different groups selected from linear or branched ($C_1$-$C_6$)alkyl, linear or branched hydroxy-($C_1$-$C_6$)alkyl, linear or branched alkox-y-($C_1$-$C_6$)alkyl, amino-($C_1$-$C_6$)alkyl in which the alkyl moiety may be linear or branched, and mono- or di-alkylaminoalkyl in which each alkyl moiety may be linear or branched and contains from 1 to 6 carbon atoms), mercapto, linear or branched ($C_1$-$C_6$)alkylthio, aminocarbonyl (the amino moiety optionally being substituted by one or two identical or different linear or branched ($C_1$-$C_6$)alkyl groups), linear or branched ($C_1$-$C_6$)alkylcarbonylamino, hydroxy-sulphonyl, linear or branched ($C_1$-$C_6$)alkylsulphonyl, or arylsulphonyl.

"Heteroaryl" is to be understood as meaning a mono- or bi-cyclic aryl group having from 5 to 12 ring members containing one, two or three identical or different hetero atoms selected from oxygen, nitrogen and sulphur, it being understood that the heteroaryl may optionally be substituted by one or more identical or different Q groups as defined hereinbefore, and that when the heteroaryl is bicyclic one of the rings may be partially hydrogenated.

According to a particularly advantageous variant, the preferred compounds of the invention are those in which the group W is attached in the 2 position of the imidazole ring.

According to another variant of the invention, the preferred compounds are those in which the substituted nitrone group

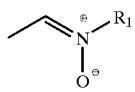

is attached in the 2 position of the imidazole ring.

Preferred substituents $R_1$ according to the invention are linear or branched ($C_1$-$C_6$)alkyl groups. Particularly advantageously, the preferred substituent RI is the tert-butyl group. Preferred substituents $R_2$ according to the invention are the hydrogen atom and linear or branched ($C_1$-$C_6$)alkyl groups.

Preferred substituents W according to the invention are aryl groups or heteroaryl groups, and more especially unsubstituted or substituted phenyl groups, unsubstituted or substituted naphthyl groups, unsubstituted or substituted pyridyl groups, unsubstituted or substituted furyl groups, unsubstituted or substituted thienyl groups, unsubstituted or substituted pyrrolyl groups, unsubstituted or substituted imidazolyl groups, unsubstituted or substituted thiazolyl groups, unsubstituted or substituted quinolyl groups and unsubstituted or substituted indolyl groups.

The preferred compound according to the invention is (Z)-α-(2-phenyl-lH-imidazol4-yl)-N-tert-butylnitrone.

The isomers and the addition salts with a pharmaceutically acceptable acid or base of the preferred compounds form an integral part of the invention.

The invention relates also to a process for the preparation of the compounds of formula (I), which is characterised in that there is used as starting material a compound of formula (II):

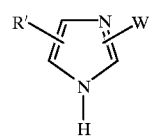

wherein W is as defined for formula (I) and R' represents a hydrogen atom or a trifluoromethyl group, which compound of formula (II), when W is attached in the 4 position of the imidazole ring and R' represents a hydrogen atom, is treated with ethyl orthoformate in the presence of para-toluenesulphonic acid to yield a compound of formula (III):

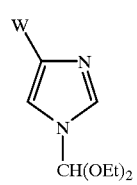

wherein W is as defined for formula (I), which compound of formula (III) is treated in the presence of a strong base with dimethylformamide, this being followed by acid hydrolysis, to yield a compound of formula (IV):

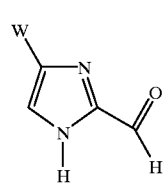

wherein W is as defined for formula (I), which compound of formula (IV) is treated with a substituted hydroxylamine of formula (V):

HO—NH—$R_1$ (V)

wherein $R_1$ is as defined for formula (I), to yield the compounds of formula (I/a), a particular case of the compounds of formula (I):

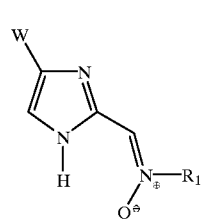

wherein W and $R_1$ are as defined for formula (I), or is treated, if desired, with an electrophilic reagent in accordance with the conventional conditions of organic synthesis to yield the compounds of formulae (IV/A) and (IV/B):

(IV/A)

(IV/B)

wherein W is as defined for formula (I) and R'$_2$ has the same meaning as R$_2$ in formula (I), except that R'$_2$ may not represent a hydrogen atom, which compounds of formulae (IV/A) and (IV/B) are separated and/or purified, if desired, according to conventional methods of separation and purification, and are then subjected to the action of a compound of formula (V) as defined hereinbefore to yield, respectively, the compounds of formulae (I/b) and (I/c), particular cases of the compounds of formula (I):

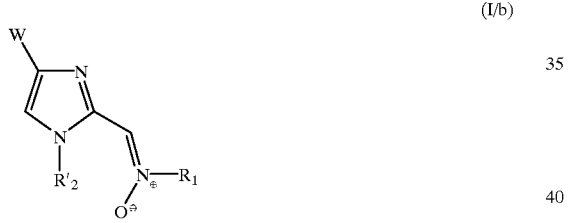

(I/b)

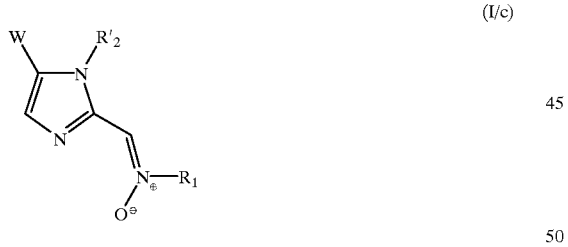

(I/c)

wherein R$_1$, R'$_2$ and W are as defined hereinbefore, or which compound of formula (II), when W is attached in the 2 position of the imidazole ring and R' represents a trifluoromethyl group

is either treated with ammonium hydroxide and then subjected to hydrolysis, or is treated with sodium hydroxide and then subjected to an N-methoxy-N-methylarmine addition step followed by a conventional reduction reaction, to yield the compounds of formula (VI):

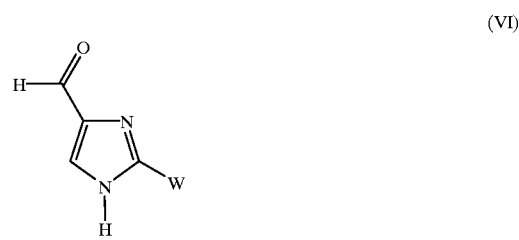

(VI)

wherein W is as defined for formula (I), which compounds of formula (VI) are subjected to the action of a compound of formula (V) as defined hereinbefore to yield the compounds of formulae (I/d), a particular case of the compounds of formula (I):

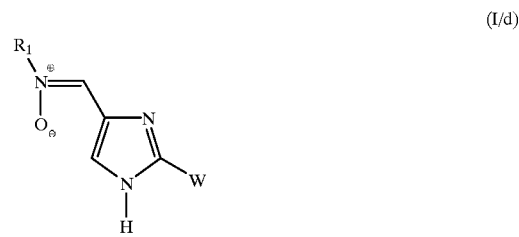

(I/d)

10 wherein R, and W are as defined for formula (I), or which compounds of formula (VI) are, if desired, treated with an electrophilic reagent, in accordance with the conventional conditions of organic synthesis, to yield the compounds of formulae (VI/A) and (VI/B):

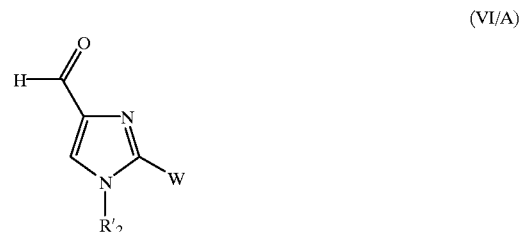

(VI/A)

(VI/B)

wherein W and R'$_2$ are as defined hereinbefore, which compounds of formulae (VI/A) and (VI/B) are separated and/or purified according to conventional methods of separation and purification, then subjected to the action of a compound of formula (V) to yield, respectively, the compounds of formulae (I/e) and (I/f), particular cases of the compounds of formula (I):

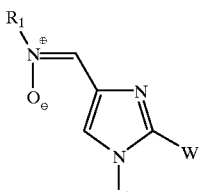

(I/e)

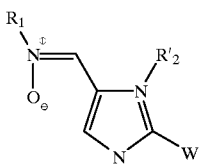

(I/f)

wherein $R_1$, $R'_2$ and W are as defined hereinbefore, the compounds of formulae (1/a) to (/f) constituting the totality of the compounds of the invention, which compounds are purified, if necessary, according to a conventional purification technique, may be separated, if desired, into their different isomers according to a conventional separation technique, and are converted, if desired, into addition salts with a pharmaceutically acceptable acid or base.

The compounds of formulae (II) and, (IV) are either commercial compounds or are obtained according to known methods of organic synthesis, such as those described in the articles *J. Med. Chem.* 1975, 18, 895, *J. Org. Chem.* 1986, 51, 3228 and *Tetrahedron. Lett.*, 1981, 3815.

The present invention relates also to pharmaceutical compositions comprising as active ingredient at least one compound of formula (I), its optical isomers or an addition salt thereof with a pharmaceutically acceptable acid or base, alone or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous), per- or trans-cutaneous, nasal, rectal, perlingual, ocular or respiratory administration, and especially tablets or dragees, sublingual tablets, sachets, gelatin capsules, lozenges, suppositories, creams, ointments, dermal gels, injectable or drinkable preparations, aerosols, eye or nose drops etc.

The dosage used varies according to the age and weight of the patient, the administration route, the nature and the severity of the disorder, and other treatments the patient may be receiving, and ranges from 10 mg to 500 mg in one or several administrations per day.

The following Examples illustrate the invention but do not limit it in any way.

The starting materials used are known products or are prepared according to known procedures.

EXAMPLE 1

(Z)-α-(2-Phenyl-1H-imidazol-4-yl)-N-tert-butylnitrone

Step A: 2-Phenyl-4-tnifluoronzetltyl-1H-imidazole

The procedure is in accordance with the operating conditions described in J. Med. Chem., 1975, 18, 895–900, using benzaldehyde as substrate.

Step B: 2-Phenyl-4-cyano-1H-imidazole

The compound obtained in Step A is subjected to the experimental protocol described in J. Org. Chem., 1986, 51, 3228–3231.

Step C: 2-Phenyl-1H-4-imidazolecarbaldelzyde

A solution containing 1.6 mnmol of the compound obtained in Step B in 3 ml of anhydrous tetrahydrofuran is placed under an argon atmosphere at −78° C. and 2.45 ml of diisobutyl-aluminium hydride (1.1M in tetrahydrofuran) are added. After 2.5 hours, 2.45 ml of reagent are again added and, after reaction for 1 hour, the temperature is adjusted to −45° C. 1 ml of methanol is then added to the reaction mixture. After stirring for 20 minutes, the temperature is increased to −20° C. and 3 ml of 1N HCl are added. Stirring is continued for 30 minutes while allowing the reaction mixture to return to ambient temperature. The solution is then diluted with dichloromethane and subsequently extracted with water. The organic phase is then dried over magnesium sulphate and subsequently concentrated under reduced pressure enabling a precipitate to be collected. The precipitate is filtered off, rinsed with dichloromethane and dried, enabling the expected product to be isolated.

Step D: (Z)-α-(2-Phenyl-1H-imidazol-4-yl)-N-tert-butylnitrone 0.05 mol of the compound obtained in Step C, 0.07 mol of N-tert-butylhydroxylamine hydrochloride and 6 g of sodium hydrogen carbonate dissolved in 50 ml of ethanol are stirred at 60° C. under an argon atmosphere for 20 hours. The reaction mixture is then brought to ambient temperature and diluted with 300 ml of dichloromethane. The organic phase is extracted with water, dried over magnesium sulphate and then concentrated under reduced pressure. The residual oil, rapidly taken up in ethyl ether, crystallises. The expected product is isolated by filtration and drying in vacuo.

Melting point: 209–210 ° C. Elemental microanalysis:

|  | C | H | N |
|---|---|---|---|
| % Calculated | 69.11 | 7.04 | 17.27 |
| % Found | 68.85 | 7.04 | 17.02 |

EXMAPLE 2

(Z)-α-[2-(4-Methylphenyl)-1H-imidazol-4-yl]-N-tert-butylnitrone

The procedure is as in Example 1, Steps A to D, using as substrate in Step A 4methyl-benzaldehyde.

Melting-point: 174–176° C. Elemental microanalysis:

|  | C | H | N |
|---|---|---|---|
| % Calculated | 70.01 | 7.44 | 16.33 |
| % Found | 69.69 | 7.57 | 16.03 |

EXAMPLE 3

(Z)-α-[2-(4-Methoyphenyl)-1H-imidazol-4-yl]-N-tert-butylnitrone

Preparation A: 4-Carboxy-2-(4-methoxyphenyl)-1H-imidazole

A solution of 3.8 g of 2-(4-methoxyphenyl)-4-trifluoromethylimidazole in 40 ml of 2N sodium hydroxide is heated at 90° C. for 1 hour with stirring. After returning to ambient temperature, the solution is adjusted to pH 6 using 2N hydrochloric acid. The precipitate is filtered off, rinsed with water and dried to yield the expected product.

Step A1: 4-(N-Methyl-N-methoxyaminocarbonyl)-2-(4-methoxyphe72yl)-1H-imidazole 15 mmol of O-benzotriazol-1-yl-N,N,N',N'-tetramethyluronium tetrafluoroborate, 49 mmol of N,N-diisopropylethylamine and 15 mmol of N-methoxymethylamine are added to a solution containing 13 mmol of the product obtained in Preparation A in 130 ml of dichloromethane. After reaction for 20 hours at ambient temperature, the reaction mixture is washed with water. The organic phase is then dried over magnesium sulphate, filtered and concentrated under reduced pressure. The residue is subsequently triturated in ether and the solid obtained is filtered off and then dried, enabling the expected product to be isolated.

Step B1: 2-(4-Methoxyphenyl)-1H-imidazole-4-carbaldehyde 0.5 g of lithium aluminium hydride is added under an argon atmosphere to a solution containing 6.1 mmol of the product obtained in Step A1 in 50 ml of tetrahydrofuran. After reaction for one hour at −10° C., 0.2 g of lithium alurninium hydride is added and stirring is carried out for one hour at 0° C. The reaction mixture is then hydrolysed by the addition of water and then using a 4N sodium hydroxide solution. After filtration of the reaction mixture, the solution is concentrated under reduced pressure. Chromatography on silica gel (dichloromethane/methanol: 9/1) enables the expected product to be isolated.

Step C1: (Z)-αa-[2-(4-Methoxyphenyl)-1H-imidazol-4-yl]-N-tert-butylnitrone

The procedure is as in Step D of Example 1, using as substrate the product obtained in Step B1.

Melting point: 198–201° C. Elemental microanalysis:

|  | C | H | N |
|---|---|---|---|
| % Calculated | 65.91 | 7.01 | 15.37 |
| % Found | 65.65 | 7.30 | 14.91 |

EXAMPLE 4

(Z)-α-[2-(4-Chlorophenyl)-1H-imidazol-4-yl]-N-tert-butylnitrone

The procedure is as in Example 1, Steps A to D, using as substrate in Step A 4-chloro-benzaldehyde.

Melting point: 212–215° C.

EXAMPLE 5

(Z)-α-[2-(4-Pyridyl)-1H-imidazol-4-yl]-N-tert-butylnitrone

The procedure is as in Example 1, Steps A to D, using as substrate in Step A 4-pyridinecarbaldehyde.

Melting point: 239–241° C. Elemental microanalysis:

|  | C | H | N |
|---|---|---|---|
| % Calculated | 63.92 | 6.60 | 22.93 |
| % Found | 63.94 | 6.58 | 23.03 |

EXAMPLE 6

(Z)-α-[2-(2-Naphthyl)-1H-imidazol-4-yl]-N-tert-butylnitrone

The procedure is as in Example 1, Steps A to D, using as substrate in Step A 2-naphthaldehyde.

Melting point: 200–202° C. Elemental microanalysis:

|  | C | H | N |
|---|---|---|---|
| % Calculated | 73.70 | 6.53 | 14.32 |
| % Found | 73.69 | 6.79 | 14.30 |

EXAMPLE 7

(Z)-α-[2-(2-Furyl)-1H-imidazol-4-yl]-N-tert-butylnitrone

The procedure is as in Example 1, Steps A to D, using as substrate in Step A 2-furylcarbaldehyde.

Melting point: 103° C. (decomposition)

EXAMPLE 8

(Z)-α-[1-Methyl-2-phenyl-1H-imidazol4-yl]-N-tert-butylnitrone

Step E: 1-Methzyl-2-phenyl-4-trifluorometlzyl-1H-imidazole

There are added at ambient temperature to a solution of 10 mmol of the compound obtained in Step A of Example 1 in 15 ml of toluene, 10 mmol of NaH and then, after 15 minutes, 10 mmol of methyl iodide diluted with 3 ml of toluene. After 2 hours, the reaction mixture is concentrated under reduced pressure, enabling an oil to be obtained which precipitates on the addition of water. Filtration enables the expected product to be isolated.

Step F: (Z)-α-[1-Methyl-2-phenyl-1H-imidazol-4-yl]-N-tert-butylnitrone

The procedure is as in Example 1, Steps B to D, using in Step B the product obtained in Step E.

EXAMPLE 9

(Z)-α-[1-Methyl-2-phenyl-1H-imidazol-5-yl]-N-tert-butylnitrone

The product is obtained as co-product in the synthesis of the compound of Example 8.

Melting point: 155–157° C. Elemental microanalysis:

|  | C | H | N |
|---|---|---|---|
| % Calculated | 70.01 | 7.44 | 16.33 |
| % Found | 70.21 | 7.47 | 16.40 |

EXAMPLE 10

(Z)-α-[2-(3Thienyl)-1H-imidazol-4-yl]-N-tert-butylnitrone

The procedure is as in Example 1, Steps A to D, using as substrate in Step A 3-thienylcarbaldehyde.

Melting point: 197–198° C. Elemental microanalysis:

|  | C | H | N | S |
|---|---|---|---|---|
| % Calculated | 57.81 | 6.06 | 16.85 | 12.86 |
| % Found | 57.85 | 6.07 | 16.42 | 13.02 |

EXAMPLE 11

(Z)-α-12-(3-Pyridyl)-1H-imidazol yll-N-trf-butylnitrone

The procedure is as in Example 1, Steps A to D, using as substrate in Step A nicotinaldehyde.

Melting point: 174–176° C. Elemental microanalysis:

|  | C | H | N |
|---|---|---|---|
| % Calculated | 63.92 | 6.60 | 22.93 |
| % Found | 63.27 | 6.67 | 22.24 |

EXAMPLE 12

(Z)-α-[2-(2-Pyridyl)-1H-imidazol-4-yl]-N-tert-butylnitrone

The procedure is as in Example 1, Steps A to D, using as substrate in Step A 2-pyridinecarbaldehyde.

Melting point: 172–173° C. Elemental microanalysis:

|  | C | H | N |
|---|---|---|---|
| % Calculated | 63.92 | 6.60 | 22.93 |
| % Found | 63.74 | 6.65 | 22.83 |

EXAMPLE 13

(Z)-α-[2-(3-Furyl)-1H-imidazol-4-yl]-N-tert-butylnitrone

The procedure is as in Example 1, Steps A to D, using as substrate in Step A 3-furylcarbaldehyde.

Melting point: 160° C.

EXAMPLE 14

(Z)-α-[2-(4-Trifluoromethylphenyl)-1H-imidazol-4-yl]-N-tert-butylnitrone

The procedure is as in Example 1, Steps A to D, using as substrate in Step A 4-(trifluoromethyl)benzaldehyde.

Melting point: 226° C. Elemental microanalysis:

|  | C | H | N |
|---|---|---|---|
| % Calculated | 57.87 | 5.18 | 13.50 |
| % Found | 57.88 | 5.12 | 13.50 |

EXAMPLE 15

(Z)-α-[2-(-Naphthyl)-1H-imidazol-4-yl]-N-tert-butylnitrone

The procedure is as in Example 1, Steps A to D, using as substrate in Step A 1-naphthylcarbaldehyde.

Melting point: 95° C. (decomposition)

EXAMPLE 16

(Z)-α-[2-(1H-Imidazol-4-yl)-1H-imidazol-4-yl]-N-tert-butylnitrone

The procedure is as in Example 1, Steps A to D, using as substrate in Step A 1H-imidazole-4-carbaldehyde.

Melting point: 220° C.

EXAMPLE 17

(Z)-α-[2-(4-Fluorophenyl)-1H-imidazol-4-yl]-N-tert-butylnitrone

The procedure is as in Example 1, Steps A to D, using as substrate in Step A 4-(fluoro)-benzaldehyde.

Melting point: 192–194° C. Elemental microanalysis:

|  | C | H | N |
|---|---|---|---|
| % Calculated | 64.35 | 6.17 | 16.08 |
| % Found | 64.49 | 6.15 | 15.88 |

EXAMPLE 18

(Z)-α-[2-(2-Chlorophenyl)-1H-imidazol-4-yl]-N-tert-butylnitrone

The procedure is as in Example 1, Steps A to D, using as substrate in Step A 2-(chloro)benzaldehyde.

Melting point: 132–134° C. Elemental microanalysis:

|  | C | H | N | Cl |
|---|---|---|---|---|
| % Calculated | 60.54 | 5.81 | 15.13 | 12.76 |
| % Found | 60.63 | 5.72 | 15.01 | 12.77 |

EXAMPLE 19

(Z)-α-[2-(3-Chlorophenyl)-1H-imidazol-4-yl]-N-tert-butylnitrone

The procedure is as in Example 1, Steps A to D, using as substrate in Step A 3-(chloro)benzaldehyde.

Melting point: 181–183° C. Elemental microanalysis:

|  | C | H | N | Cl |
|---|---|---|---|---|
| % Calculated | 60.54 | 5.81 | 15.13 | 12.76 |
| % Found | 60.52 | 5.91 | 14.96 | 12.90 |

EXAMPLE 20

(Z)-α-2-(4-Nitrophenyl)-1H-imidiazol-4-yl-N-tert-butylnitrone

The procedure is as in Example 1, Steps A to D, using as substrate in Step A 4-(nitro)-benzaldehyde.

Melting point: 253° C. Elemental microanalysis:

|  | C | H | N |
| --- | --- | --- | --- |
| % Calculated | 58.33 | 5.59 | 19.43 |
| % Found | 57.95 | 5.51 | 18.99 |

EXAMPLE 21

(Z)-α-[2-(4-Dimethylaminophenyl)-1H-N-imidazol-4-yl]-N-tert-butylnitrone

The procedure is as in Example 1, Steps A to D, using as substrate in Step A 4-(dimethylamino)benzaldehyde.
Melting,point: 190–192° C. Elemental microanalysis:

|  | C | H | N |
| --- | --- | --- | --- |
| % Calculated | 67.11 | 7.74 | 19.56 |
| % Found | 66.90 | 7.78 | 19.30 |

EXAMPLE 22

(Z)-α-[2-(2-Thiazolyl)-1H-imidazol-4-yl]-N-tert-butylnitrone

The procedure is as in Example 1, Steps A to D, using as substrate in Step A 2-(thiazolyl)carbaldehyde.
Melting point: 170° C.

EXAMPLE 23

(Z)-α-[2-(3,4Dimethoyphenyl)-1H-imidazol-4-yl]-N-tert-butylnitrone

The procedure is as in Example 1, Steps A to D, using as substrate in Step A (3,4-dimethoxy)benzaldehyde.
Melting point: 202–205° C.

EXAMPLE 24

(Z)-α-[2-(3,4-Methylenedioxyphenyl)-1H-imidazol-4-yl]-N-tert-butylnitrone

The procedure is as in Example 1, Steps A to D, using as substrate in Step A (3,4-methylenedioxy)benzaldehyde.

EXAMPLE 25

(Z)-α-(2-Phenethyl-1H-imidazol-4-yl)-N-tert-butylnitrone

The procedure is as in Example 1, Steps A to D, using as substrate in Step A 3-phenylpropionaldehyde.

EXAMPLE 26

(Z)-α-[2-(5 Nitro-3-thienyl)-1H-imidazol-4-yl]-N-tert-butylnitrone

The procedure is as in Example 1, Steps A to D, using as substrate in Step A 2-nitrothiophene-4-carbaldehyde.

EXAMPLE 27

(Z)-α-[2-(5-Methyl-2-thieny)-1H-imidazol-4-yl]-N-tert-butylnitrone

The procedure is as in Example 1, Steps A to D, using as substrate in Step A 5-methylthiophene-2-carbaldehyde.

EXAMPLE 28

(Z)-α-[2-(4-Methylthiophenyl)-1H-imidazol-4-yl]-N-tert-butylnitrone

The procedure is as in Example 1, Steps A to D, using as substrate in Step A 4-(methylthio)benzaldehyde.

EXAMPLE 29

(Z)-α-[2-(1-Methyl-1H-pyrrol-2-yl)-1H-imidazol-4-yl]-N-tert-butylnitrone

The procedure is as in Example 1, Steps A to D, using as substrate in Step A 1-methyl-pyrrole-2-carbaldehyde.

EXAMPLE 30

(Z)-α-[2-(1-Methyl-1H-indol-3-yl)-1H-imidazol-4-yl]-N-tert-butylnitrone

The procedure is as in Example 1, Steps A to D, using as substrate in Step A 1-methyl-indole-3-carbaldehyde.

EXAMPLE 31

(Z)-α-[2-(3-Methyl-benzo[b]thiophen-2-yl)-1H-imidazol-4-yl]-N-tert-butylnitrone

The procedure is as in Example 1, Steps A to D, using as substrate in Step A 3-methylbenzo[b]thiophene-2-carbaldehyde.

EXAMPLE 32

(Z)-α-[2-(4-Methoxy-1-naphthyl)-1H-imidazol-4-yl]-N-tert-butylnitrone

The procedure is as in Example 1, Steps A to D, using as substrate in Step A 4methoxy-1-naphthaldehyde.

EXAMPLE 33

(Z)-α-[2-(5-Ethyl-2-furyl)-1H-imidazol-4-yl]-N-tert-butylnitrone

The procedure is as in Example 1, Steps A to D, using as substrate in Step A 5-ethylfurfural.

EXAMPLE 34

(Z)-α-[2-(2,5-Dimethyl-1-phenyl-1H-pyrrol-3-yl)-1H-imidazol-4-yl]-N-tert-butylnitrone The procedure is as in Example 1, Steps A to D, using as substrate in Step A 2,5-dimethyl-1-phenylpyrrole-3-carbaldehyde.

EXAMPLE 35

(Z)-α-[2-(4-Biphenyl)-1H-imidazol-4-yl]-N-tert-butylnitrone

The procedure is as in Example 1, Steps A to D, using as substrate in Step A 4-phenyl-benzaldehyde.

EXAMPLE 36

(Z)-α-[2-(Benzo[b]furan-2-yl)-1H-imidazol-4-yl]-N-tert-butylnitrone

The procedure is as in Example 1, Steps A to D, using as substrate in Step A benzo[b]furan-2-carbaldehyde.

EXAMPLE 37

(Z)-α-[2-(4-Acetoxy-3-metboyphenyl)-1H-imidazol-4-yl ]-N-tert-butylnitrone

The procedure is as in Example 1, Steps A to D, using as substrate in Step A 4-acetoxy-3-methoxybenzaldehyde.

EXAMPLE 38

(Z)-α-[2-(3-Quinolinyl)-1H-imidazol-4-yl]-N-tert-butylnitmne

The procedure is as in Example 1, Steps A to D, using as substrate in Step A quinoline-3-carbaldehyde.

EXAMPLE 39

(Z)-α-[2-(2,3-Dihydro1H-indolfyl)-1H-imidazol-4-yl]-N-tert-butylnitrone

The procedure is as in Example 1, Steps A to D, using as substrate in Step A indoline-3-carbaldehyde.

EXAMPLE 40

(Z)-α-(4-Phenyl-1H-imidazol-2-yl)-N-tert-butylnitrone

Step A2: 4-Phenyl-1-triphenylmethyl-1H-imidazole 7.6 mmol of triphenylmethyl chloride in 150 ml of dimethylformamide are added, under an argon atmosphere, to a solution of 6.9 mnmol of 4-phenyl-1H-imidazole in 50 ml of dimethylformamide and 10 ml of triethylamine. The solution is stirred for 4 hours at ambient temperature. After the addition of water, the precipitate obtained is triturated in ethyl ether, filtered and then dried, enabling the product obtained to be isolated.

Step B2: 2-Formyl-4-phenyl-1-triphenylmetltyl-1H-imidazole 25.7 mmol of the product obtained in Step A2 are stirred at 0° C. in 250 ml of anhydrous tertrahydrofuran, under an argon atmosphere, and then 25 ml of n-butyllithium (1.6 M in hexane) are slowly added. After reaction for 2 hours, 8 ml of dimethylformarnide are added. After stirring for 2 hours at ambient temperature, 250 ml of water are added and then the tertrahydrofuran is evaporated off under reduced pressure. Extraction of the aqueous phase using dichloromethane, following by concentration, after drying, of the organic phase, enables an oil to be obtained which crystallises in ethyl ether, yielding the expected product.

Step C2: (Z)-α-(4-Phenyl-1-triphenylmethyl-1H-imidazol-2-yl)-N-tert-butylnitrone The procedure is as in Step D of Example 1, using as substrate the product obtained in Step B2.

Step D2: (Z)-α-(4-Phenyl-1H-imidazol-2-yl)-N-tert-butylnitrone 11.5 mol of the product obtained in Step C2 are heated at reflux in 60 ml of an ethanol solution containing 5 ml of acetic acid. After reaction for 5 hours, the reaction mixture is concentrated under reduced pressure, taken up in dichloromethane, washed with a 5% sodium hydrogen carbonate solution and then with water. After drying the organic phase over magnesium sulphate and concentration under reduced pressure, the resulting residual oil is triturated in ethyl ether enabling the expected product to be isolated in crystalline form.

Melting point: 166° C. Elemental microanalysis:

|  | C | H | N |
|---|---|---|---|
| % Calculate | 69.11 | 7.04 | 17.27 |
| % Found | 69.07 | 7.02 | 17.15 |

EXAMPLE 41

(Z)-α-(1-Benzyl-2-phenyl-1H-imidazol-4-yl)N-tert-butylnitrone

Step E2: 1-Benzyl-2-phenyl-4-(trifluoromethyl)-1H-imidazole

The procedure is as in Step E of Example 8, using benzyl chloride as reagent.

Step F2: (Z)-α-(1-Benzyl-2-phenyl-1H-imidazol-4-yl)-N-tert-butylnitrone

The procedure is as in Step F of Example 8, using as substrate the compound obtained in Step E2.

EXAMPLE 42

(Z)-α-[2-(2,3-Dihydro-1,4-benzodioxin-6-yl)-1H-imidazol-4-yl]-N-tert-butylnitrone The procedure is as in Example 1, Steps A to D, using as substrate in Step A, 2,3-dihydro-1,4-benzodioxine-6-carbaldehyde.

EXAMPLE 43

(Z)-α-[2-(2,2-Difluoro-1,3-benzodioxol-5yl)-1H-imidazol-4-yl]-N-tert-butylnitrone The procedure is as in Example 1, Steps A to D, using as substrate in Step A, 2,2-difluoro-1,3-benzodioxol-5-carbaldehyde.

Pharmacological Study of the Compounds of the Invention

EXAMPLE 44

Cytotoxicity test using L-homocysteine

This test enables the in vitro evaluation of the neuroprotective properties of the test compounds by determining their capacity to combat the cytotoxicity caused by the exposure of murine HT 22 hippocampal cells to L-homocysteine (*Neuron*. 2, 1989, 1547–1558).

Murine HT 22 hippocampal cells in culture are preincubated for 24 hours in the presence of seven concentrations (5, 10, 25, 50, 75, 100 and 200 μM) of the "anti-oxidation" agent studied. The cell cultures are then exposed for 24 hours to 2 mM L-homocysteine in the presence or in the absence of anti-oxidation agents. The cytotoxicity is evaluated by the 3-(4,5-dimethylthiazol-2-yl)-2,5-diphenyl-tertrazolium bromide reduction method (*Immunol. Methods*, 1983, 65 55–63). The results are expressed as $PC_{50}$, the concentration that represents 50% protection compared with the cytotoxicity measured in the cell cultures in the absence of anti-oxidation agents. In this test, the compound of Example 1 has a $PC_{50}$ of 88 μM.

EXAMPLE 45

Lethality Test

This test enables the in vivo determination of the neuroprotective properties of the test compounds by measuring their capacity to combat the lethality induced in the mouse by the intracerebroventricular administration of tert-butylhydroperoxide, an oxidizing agent capable of causing neurodegeneracies of the apoptotic type (*Free Radical Biol. Med.*, 1993, 15 195–202 and *Mol. Chem. Neuropathol.*, 1991, 26 95–106).

Intracerebroventricular administration of tert-butylhydroperoxide (1 μl of a 70% solution) induces lethality in the male NMRI mouse (30–35 g). The lethality is measured two hours after the administration of tert-butylhydroperoxide and is expressed as a percentage of protection compared with the lethality in the animals that have been given the carrier of the "anti-oxidation" agents studied. The latter are administered by the intraperitoneal route in a dose of 150 mg/kg 30 minutes before the administration of tert-butylhydroperoxide. In this test, the compound of Example 1 provides 80% protection.

EXAMPLE 46

Evaluation of the Effects of the Anti-oxidation Agents on Body Temperature

All of the anti-oxidation compounds described in the literature are neuroprotectors at doses that cause hypothermia, which constitutes a drawback when they are administered.

The body temperature in adult male NMRI mice (25–30 g) is measured using a rectal probe 30, 60, 90 and 120 minutes after the administration by the intraperitoneal route of the anti-oxidation agents studied in a dose of 150 mg/kg. The results are expressed as the average maximum difference in temperature determined in the treated animals compared with the control animals, which have received only the carrier (20 ml/kg) of the anti-oxidation agents studied. In this test, the compound of Example 1 does not induce associated hypothermia, a result which is especially surprising and interesting for that category of compound.

EXAMPLE 47

Transitory Global Cerebral Ischaemia Test in the Rat

This test enables evaluation of the neuroprotective (anti-ischaenic) properties of the test compounds. It was carried out according to the method of Pulsinelli and Brierley (*Stroke*, 10, 1979, 267–272).

Adult male Wistar rats weighing 280–320 g are anaesthetised with pentobarbital (60 mg/kg i.p.). The two vertebral arteries are permanently occluded by cauterisation, and atraumatic clamps are placed around the 2 common carotids. The next day, transitory global ischaemia is induced in the conscious rat by tightening the carotid clamps for 10 minutes. The clamping of the carotids results in a loss of the righting reflex of the animals in the minute that follows clamping and for the entire duration of the ischaemia. The products studied are administered by the intraperitoneal route 30 minutes before the carotids are clamped, using the appropriate solvent (2 ml/kg). The control animals are given only the solvent of the products studied. Seven days after the ischaemia, the animals are sacrificed and the brains are removed and stored at −30° C. Frontal brain sections (7 gM) are taken in the frozen state and stained with eosin-hematoxylin. The neurodegeneracy of the hippocampal neurones (layer CA1) induced by the ischaemia is measured by a neurone count under an optical microscope. The parameter measured is the number of viable neurones expressed as a percentage of that determined in the non-ischaemised control animals.

At a dose of 100 mg/kg i.p., tert-butylphenylnitrone reduces hippocampal neurone death in the ischaemised animals by a factor of 2.3.

At a dose of 75 mg/kg i.p., the compound of Example 14 reduces hippocampal neurone death in the ischaemised animals by a factor of 3.

EXAMPLE 48

Pharmaceutical Composition

Formulation for the preparation of 1000 tablets each comprising 20 mg of active ingredient

| | |
|---|---|
| compound of Example 1 | 20 g |
| hydroxypropylcellulose | 3 g |
| polyvinylpyrrolidone | 3 g |
| wheat starch | 10 g |
| lactose | 100 g |
| magnesium stearate | 3 g |

We claim:

1. A compound selected from those of formula (I):

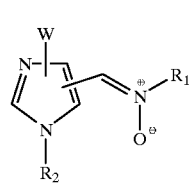

(I)

wherein:
- W represents aryl, aryl-($C_1$–$C_6$)alkyl in which alkyl is linear or branched, heteroaryl or heteroaryl-($C_1$–$C_6$)alkyl in which alkyl is linear or branched,
- $R_1$ represents linear or branched ($C_1$–$C_6$)alkyl, linear or branched ($C_2$–$C_6$)alkenyl linear or branched ($C_2$–$C_6$)alkynyl, aryl, cycloalkyl, aryl-($C_1$–$C_6$)alkyl in which alkyl is linear or branched, or cycloalkyl-($C_1$–$C_6$)alkyl in which alkyl is linear or branched,
- $R_2$ represents hydrogen, linear or branched ($C_1$–$C_6$)alkyl, aryl, aryl-($C_1$–$C_6$)alkyl in which alkyl is linear or branched, cycloalkyl, cycloalkyl-($C_1$–$C_6$)alkyl in which alkyl is linear or branched, heterocycloalkyl, heterocycloalkyl-($C_1$–$C_6$)alkyl in which alkyl is linear or branched, heteroaryl, heteroaryl-($C_1$–$C_6$)alkyl in which alkyl is linear or branched, linear or branched ($C_1$–$C_6$)acyl, linear or branched ($C_1$–$C_6$) alkylsulphonyl, arylsulphonyl, aryl-($C_1$–$C_6$) alkylsulphonyl in which alkyl is linear or branched, or linear or branched ($C_2$–$C_6$)alkenyl, their isomers, and addition salts thereof with a pharmaceutically-acceptable acid or base.

2. A compound of claim 1, wherein W is attached in the 2 position of the imidazole ring.

3. A compound of claim 1, wherein the substituted nitrone

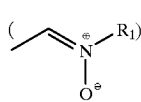

is attached in the 2 position of the imidazole ring.

4. A compound of claim 1, wherein $R_1$ represents linear or branched ($C_1$–$C_6$)alkyl.

5. A compound of claim 1, wherein $R_1$ represents tert-butyl.

6. A compound of claim 1, wherein W represents optionally substituted aryl, or optionally substituted heteroaryl.

7. A compound of claim 1, wherein W represents unsubstituted or substituted phenyl, unsubstituted or substituted naphthyl, unsubstituted or substituted pyridyl, unsubstituted or substituted furyl, unsubstituted or substituted thienyl, unsubstituted or substituted pyrrolyl, unsubstituted or substituted imidazolyl, unsubstituted or substituted thiazolyl, unsubstituted or substituted quinolyl, or unsubstituted or substituted indolyl.

8. A compound of claim 1, wherein $R_2$ represents hydrogen or linear or branched $(C_1-C_6)$alkyl.

9. A compound of claim which is (Z)-α-(2-phenyl-1H-imidazol-4-yl)-N-tert-butylnitrone.

10. A method for treating a living body afflicted with a condition requiring an anti-oxidation agent comprising the step of administering to the living body an amount of a compound of claim 1 which is effective for alleviation of said condition.

11. A method for treating a living body afflicted with cognitive disorders associated with cerebral ageing or neurodegenerative disorders, and/or acute and progressive neurodegenerative disorders, comprising the step of administering to the living body an amount of an anti-oxidation agent of claim 1, which is effective for alleviation of said condition.

12. A pharmaceutical composition useful as an anti-oxidation agent comprising as active principle an effective amount of a compound of claim 1, in combination with one or more pharmaceutically-acceptable excipients or carriers.

* * * * *

UNITED STATES PATENT AND TRADEMARK OFFICE
CERTIFICATE OF CORRECTION

PATENT NO. : 6,034,250
DATED : Mar. 7, 2000
INVENTOR(S) : S. Goldstein, A. Dhainaut, A. Tizot, B. Lockhart, P. Lestage Page 1 of 4

It is certified that error appears in the above-indentified patent and that said Letters Patent is hereby corrected as shown below:

Column 2, line 47: At the end of the line, "tezi-" should read: -- tert- --.

Column 3, line 15: "alkox-y-$(C_1-C_6)$" should read -- alkoxy-$(C_1-C_6)$ --.

Column 3, line 47: "RI" should read -- $R_1$ --.

Column 6, line 1: "methylarmine" at the beginning of the line, should read -- methylamine --.

Column 6, line 35: "10" at the beginning of the line should be deleted.

Column 7, line 21: "(1/a) to (/f)" should read -- (I/a) to (I/f) --.

Column 7, line 60: "tnifluoronzetltyl-" should read -- trifluoromethyl- --.

Column 8, line 1: "imidazolecarbaldelzyde" should read: -- imidazolecarbaldehyde --. Page 11, line 1

Column 8, line 2: "1.6 mnmol" should read: -- 1.6 mmol --.

Column 8, line 58: "Methoyphenyl)-" should read -- Methoxyphenyl)- --.

UNITED STATES PATENT AND TRADEMARK OFFICE
CERTIFICATE OF CORRECTION

PATENT NO. : 6,034,250
DATED : Mar. 7, 2000
INVENTOR(S) : S. Goldstein, A. Dhainaut, A. Tizot, B. Lockhart, P. Lestage Page 2 of 4

It is certified that error appears in the above-indentified patent and that said Letters Patent is hereby corrected as shown below:

Column 9, line 2: "methoxyphe72yl)-" should read
-- methoxyphenyl)- --.

Column 9, line 28: "(Z)-αa-" should read:
-- (Z)-α- --.

Column 10, line 26: "Methzyl-" should read:
-- Methyl- --; and "trifluorometlzyl-" should
read -- trifluoromethyl- --.

Column 11, line 12: "imidazol yll-N-trf-" should read
-- imidazol-4-yl]-N-tert- --.

Column 11, line 62: "(Z)- [2-(-Naphthyl)-" should read
-- (Z)-α-[2-(1-Naphthyl)- --.

Column 12, line 63(approx.): "(Z)-α-2-(4-Nitrophenyl)-1H-imidiazol-" should read:
--  (Z)-α-[2-(4-Nitrophenyl)-1H-imidazol- --.

Column 13, line 12: "-1H-N-imidazol-" should read
-- -1H-imidazol- --.

Column 13, line 35: "(3,4Dimethoyphenyl)-" should read
-- (3,4-Dimethoxyphenyl)- --.

Column 13, line 63: "-2-thieny)-" should read
-- -2-thienyl)- --.

UNITED STATES PATENT AND TRADEMARK OFFICE
CERTIFICATE OF CORRECTION

PATENT NO. : 6,034,250
DATED : Mar. 7, 2000
INVENTOR(S) : S. Goldstein, A. Dhainaut, A. Tizot, B. Lockhart, P. Lestage Page 3 of 4

It is certified that error appears in the above-indentified patent and that said Letters Patent is hereby corrected as shown below:

Column 15, line 3: "3-metboyphenyl)-" should read -- 3-methoxyphenyl)- --.

Column 15, line 12: "butylnitmne" should read -- butylnitrone --.

Column 15, line 18: "1H-indolfyl)-" should read -- -1H-indol-3-yl)- --.

Column 15, line 32: "6.9 mnmol" should read -- 6.9 mmol --.

Column 15, line 38: "triphenylmetltyl-" should read -- triphenylmethyl- --.

Column 15, line 44: "dimethylformarnide" should read -- dimethylformamide --.

Column 16, line 57: "65 55-63)." should read -- 65, 55-63). --.

Column 17, line 5: "15 195-202" should read -- 15, 195-202 --.

Column 17, line 6: "26 95-106)." should read -- 26, 95-106). --.

Column 17, line 43: At the beginning of the line, "ischaenic)" should read -- ischaemic) --.

Column 17, line 60: "(7gM)" should read -- (7µM) --.

UNITED STATES PATENT AND TRADEMARK OFFICE
CERTIFICATE OF CORRECTION

PATENT NO. : 6,034,250
DATED : Mar. 7, 2000
INVENTOR(S) : S. Goldstein, A. Dhainaut, A. Tizot B. Lockhart, P. Lestage It is certified that error appears in the above-indentified patent and that said Letters Patent is hereby corrected as shown below:

Column 18, line 39: "$(C_2-C_6)$alkenyl" should read -- $(C_2-C_6)$alkenyl, --.

Column 18, line 54: At the beginning of the line, "their" should be -- its --.

Column 19, line 15: "claim" should read -- claim 1 --.
    Page 28, line 21

Column 19, line 18: "agent" should read -- agent, --.

Signed and Sealed this

Twenty-sixth Day of December, 2000

Attest:

Q. TODD DICKINSON

Attesting Officer            Director of Patents and Trademarks